United States Patent [19]

Faraz et al.

[11] Patent Number: 5,766,186
[45] Date of Patent: Jun. 16, 1998

[54] SUTURING DEVICE

[75] Inventors: Ali Faraz, Coquitlam; Shahram Payandeh, Port Moody, both of Canada

[73] Assignee: Simon Fraser University, Burnaby, Canada

[21] Appl. No.: 759,963

[22] Filed: Dec. 3, 1996

[51] Int. Cl.⁶ .................................................. A61B 17/04
[52] U.S. Cl. ............................................ 606/145; 606/223
[58] Field of Search .................................... 606/139, 144, 606/145, 223; 112/80.3, 169

[56] References Cited

U.S. PATENT DOCUMENTS

| | | |
|---|---|---|
| 4,027,608 | 6/1977 | Arbuckle . |
| 4,235,178 | 11/1980 | Ackermann . |
| 4,345,601 | 8/1982 | Fukuda . |
| 4,440,172 | 4/1984 | Langer . |
| 4,524,771 | 6/1985 | Troutman et al. . |
| 4,724,840 | 2/1988 | McVay et al. . |
| 4,747,358 | 5/1988 | Moll et al. . |
| 4,841,888 | 6/1989 | Mills et al. . |
| 5,037,433 | 8/1991 | Wilk et al. . |
| 5,100,421 | 3/1992 | Christoudias . |
| 5,281,235 | 1/1994 | Haber et al. . |
| 5,282,806 | 2/1994 | Haber et al. . |
| 5,306,281 | 4/1994 | Beurrier ................................ 606/144 |
| 5,308,353 | 5/1994 | Beurrier ................................ 606/144 |
| 5,364,408 | 11/1994 | Gordon . |
| 5,411,481 | 5/1995 | Allen et al. . |
| 5,437,681 | 8/1995 | Meade et al. . |
| 5,439,469 | 8/1995 | Heaven et al. . |
| 5,454,823 | 10/1995 | Richardson et al. . |
| 5,458,609 | 10/1995 | Gordon et al. . |
| 5,470,338 | 11/1995 | Whitfield et al. . |

*Primary Examiner*—Gary Jackson
*Attorney, Agent, or Firm*—Oyen Wiggs Green & Mutala

[57] ABSTRACT

A suturing device is disclosed. The suturing device has particular application in surgery and is readily adaptable for use in laparoscopic surgery. The suturing device has an arcuate needle which is circulated around a circular path. The needle is driven by a drive belt which bears against the rear faces of a pair of closely spaced guides. Idler rollers behind the belt pinch the needle against the guides and slightly deform the drive belt. The needle is firmly gripped between the belt and the guides. The guides and the needle each subtend an angle of about 240°. The motion of the needle is reversible. A surgeon can regulate the motion of the needle by turning a wheel with a fingertip. A pair of tissue gripping jaws are provided to hold tissues in place during suturing. The suturing device may be used to form a knot after a suture has been placed.

22 Claims, 8 Drawing Sheets

SUTURING DEVICE

FIELD OF THE INVENTION

This invention relates to suturing devices which include a curved suturing needle and a drive mechanism for circulating the needle around a closed path to drive the needle through tissue or other materials to be sutured. Suturing devices according to the invention have particular application for surgical suturing.

BACKGROUND OF THE INVENTION

In surgery it is necessary for a surgeon to suture tissues together and to create knots in the sutures to hold the sutures in place. A wide variety of devices have been designed to assist the surgeon in suturing. With the advent of laparoscopic surgery such suturing devices have become more necessary to the surgeon because laparoscopic surgery often requires sutures to be placed inside body cavities in places which are hard to reach. It can be very difficult to place such sutures manually using traditional laparoscopic surgery techniques which include manipulating a needle through a series of complex movements with a pair of endoscopic graspers (or "needle drivers").

There are several previous suturing devices which include an arcuate needle which is circulated around a path by a driving mechanism. These include Andersson, U.S. Pat. No. 4,557,265 and Brunk, U.S. Pat. No. 4,899,746. Both Andersson and Brunk drive an arcuate needle by means of one or more rollers which frictionally contact the needle. The rollers contact only small areas on the needle's surface.

Beurrier, U.S. Pat. Nos. 5,308,353 and 5,306,281 describe suturing mechanisms in which an arcuate needle is driven by a belt which contacts the radially outer face of the needle. A number of teeth project outwardly from the needle to engage the belt, thereby preventing the needle from slipping relative to the belt. The Beurrier devices suffer from the disadvantages that the direction of needle rotation cannot readily be reversed during operation and the teeth on the needle can damage the drive belt and the tissues being sutured.

SUMMARY OF THE INVENTION

This invention provides a suturing device wherein an arcuate needle is driven by a belt. In particular, the invention provides a suturing device comprising: a pair of arcuate guides separated by a narrow slit; a first guide roller near a first end of the guides; a second guide roller near a second end of the guides; a drive pulley; a belt passing around the first, second rollers and positively engaged with the drive pulley, the belt having an outer surface in pressing engagement with rear faces of the guides; an arcuate suturing needle having a common arc with the guides; at least one idler roller between the guide rollers for further compressing the belt against the rear faces of the guides; and means for circulating the belt to circulate the suturing needle around the arcuate guides. The guides subtend an angle greater than about 200 degrees. The suturing needle is received between the belt and the guides and has an outer surface frictionally engaged with the outer surface of said belt.

BRIEF DESCRIPTION OF THE DRAWINGS

In drawings which illustrate non-limiting preferred embodiments of the invention.

DETAILED DESCRIPTION OF PREFERRED EMBODIMENTS OF THE INVENTION

Figure 1:
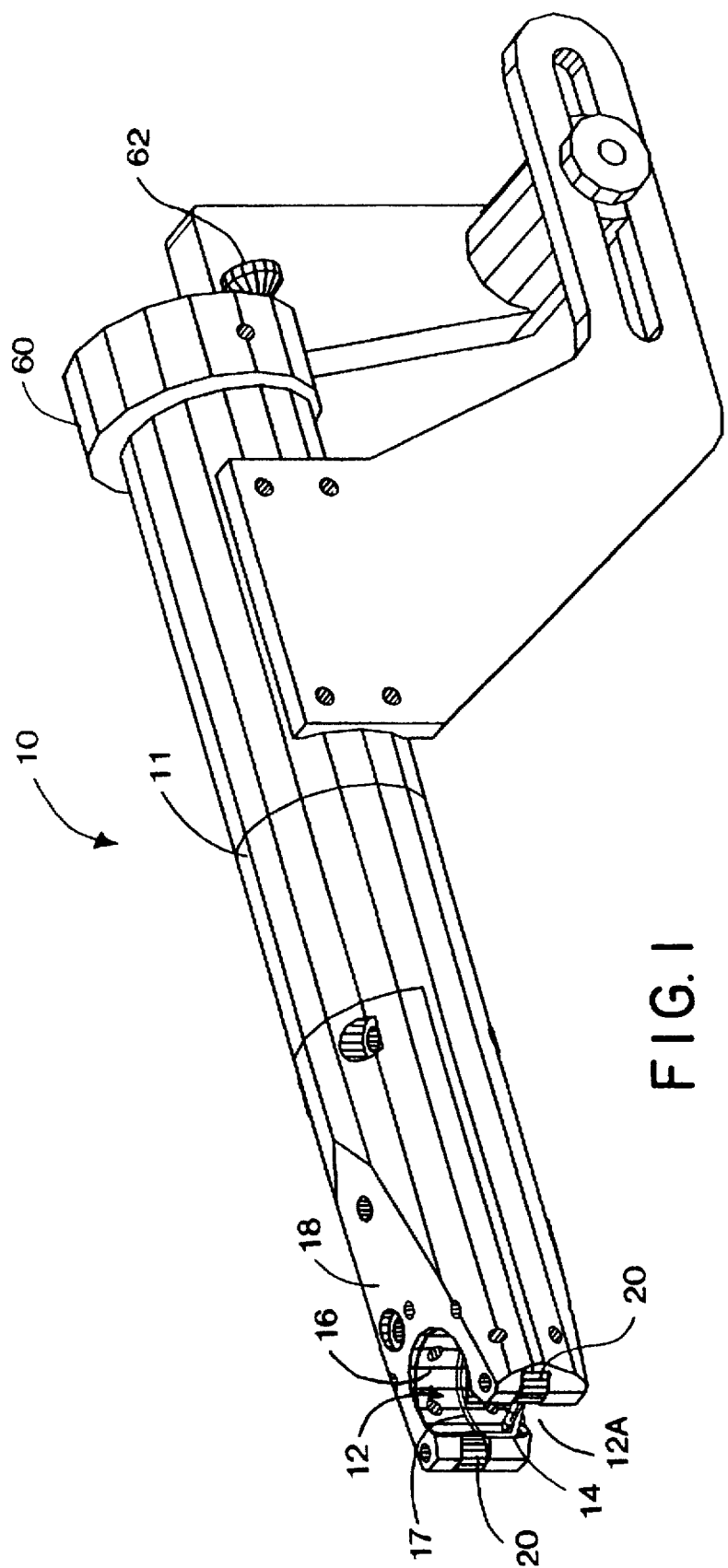
FIG. 1 is a perspective view of a suturing device according to the invention.
Figure 2:
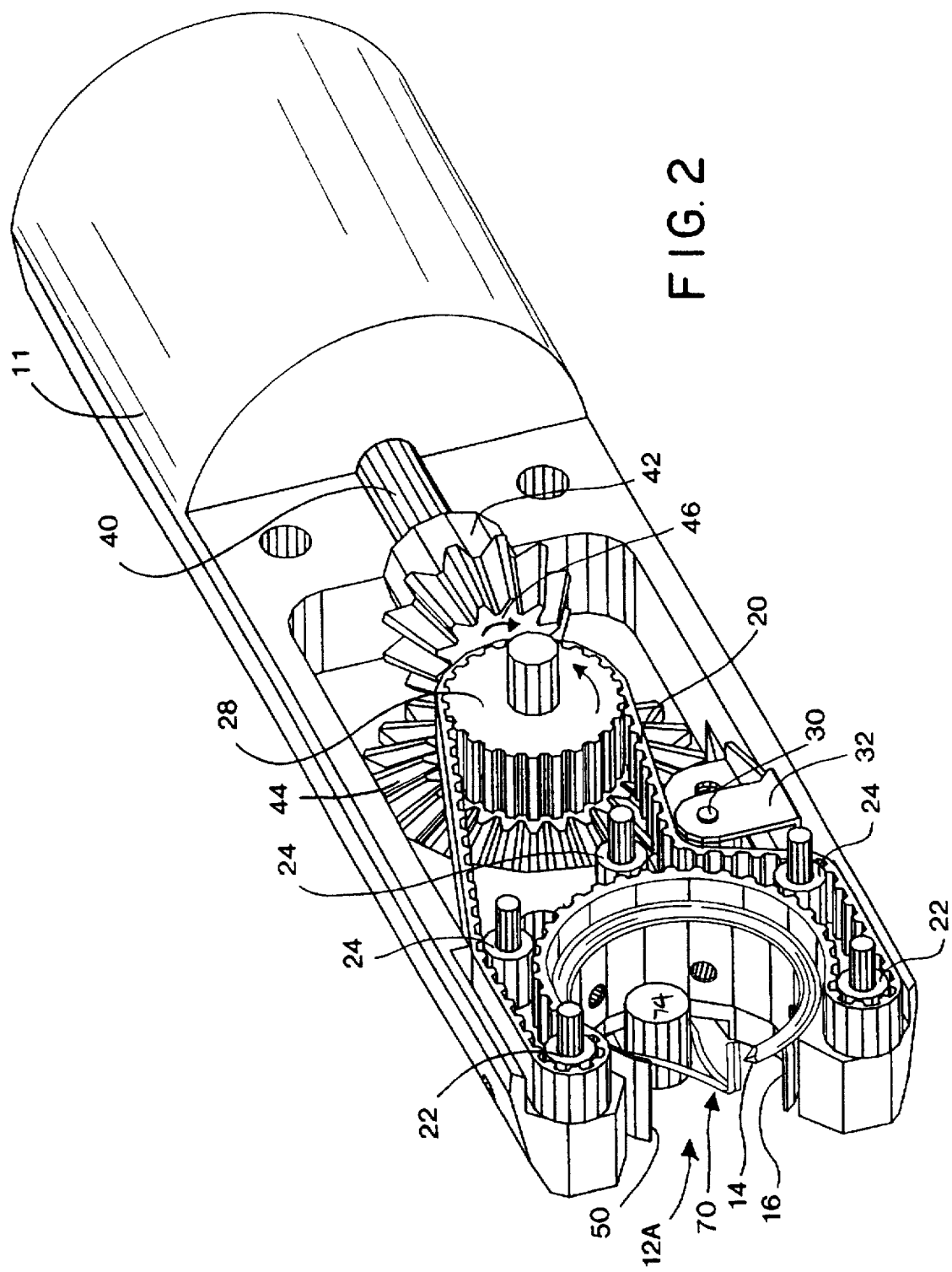
FIG. 2 is a partially cut away perspective view illustrating the internal mechanism of a preferred embodiment for the suturing device of FIG. 1.
Figure 3:
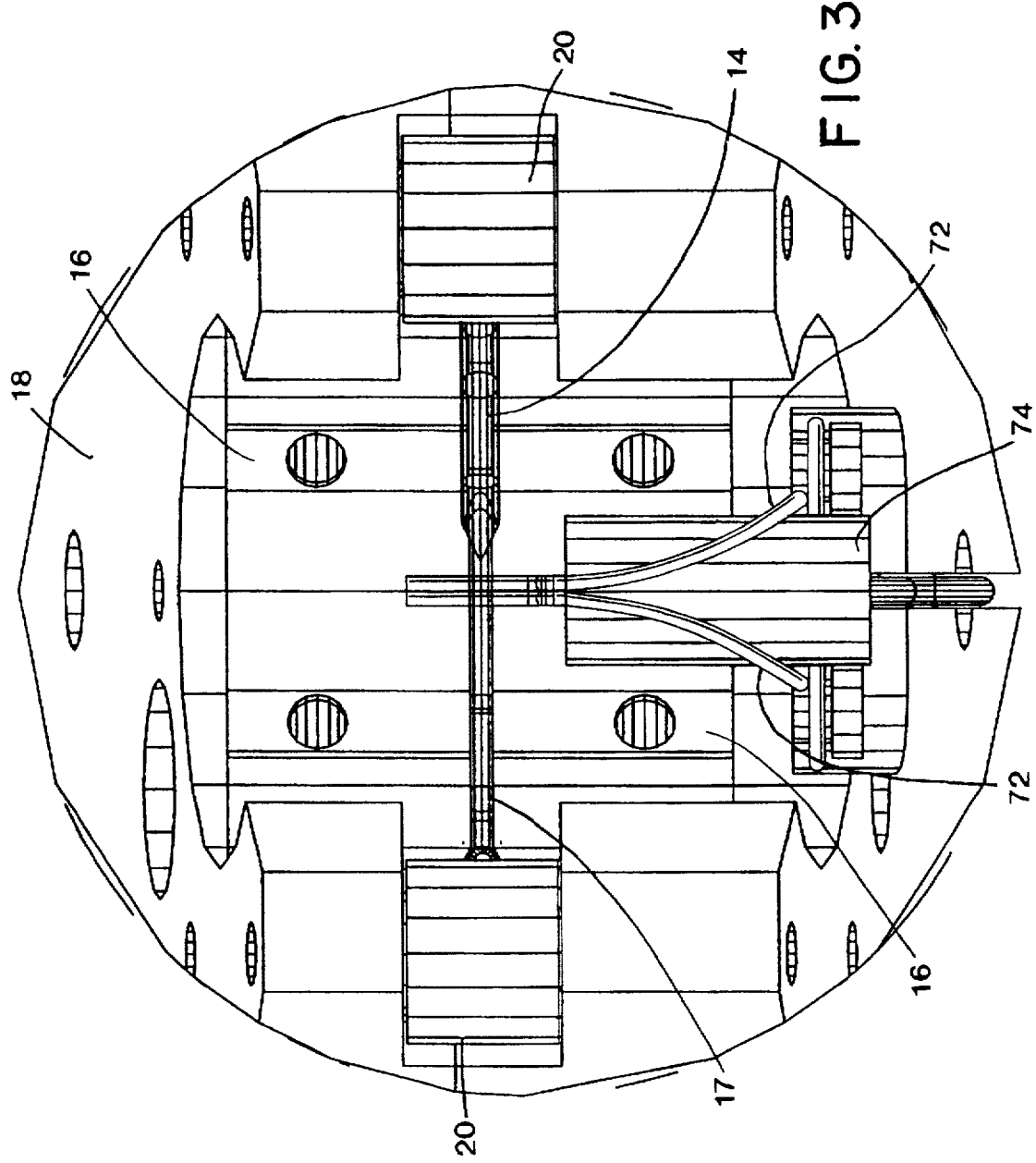
FIG. 3 is a front elevational view of the suturing device of FIG. 1.

As shown in FIG. 1, a suturing device 10 has a longitudinally extending body 11 having a transverse circular opening 12 at its end. An arcuate needle 14 can be circulated around a closed path (indicated in dotted outline by 13) enclosing opening 12 by means of a drive mechanism which is described below.

Suture material 15 is supplied to needle 14 in a suitable manner either along the side of body 11 or through a channel extending along body 11. A light tension is preferably applied to suture material 15 to prevent suture material 15 from becoming tangled. Suture material 15 is affixed to a trailing end of needle 14 by any suitable means and is conveniently attached to needle 14 in the same manner that suturing material is attached to conventional suturing needles.

When device 10 is to be used in laparoscopic surgery then body 11 is preferably cylindrical, elongated and dimensioned to fit through a standard-sized trocar. Body 11 is preferably at least 300 mm in length to permit suturing device 10 to easily reach through a trocar to the surgical site. It will be readily apparent to those skilled in the art that a suturing device as described herein may be used in surgery generally, not just in laparoscopic surgery, and may be used in non-surgical suturing and knotting applications.

A surgeon can use suturing device 10 as described below and shown in FIGS. 7A to 7C to suture two pieces of tissue together. The suturing device can also be used as described below and shown in FIGS. 8A to 8C to tie knots in suture material 15. Other modes of use of suturing device 10 will be readily apparent to skilled surgeons.

Needle 14 is held in position around opening 12 by a pair of thin guides 16 which are separated by a slit 17 wide enough to allow the passage of suture material 15 but not wide enough to allow needle 14 to escape. Preferably guides 16 subtend an arc of at least about 200° preferably more than 230°, and most preferably about 240°. Preferably needle 14 also subtends an arc of at least about 200°, preferably more than 230°, and most preferably about 240°. Thus, needle 14 cannot unintentionally become disengaged from suturing device 10. The entrance 12A to opening 12 typically subtends an arc of about 120° so that it is large enough to accept tissues to be sutured.

Needle 14 slides on guides 16 along slit 17. Slit 17 serves to guide needle 14 and also allows suture material 15 to follow needle 14 without becoming wrapped around any part of device 10. The motion of needle 14 is driven by a belt 20. Belt 20 is directed around the rear face of guides 16 by a pair of guide rollers 22 which are located on either side of entrance 12A. Several, preferably two or more idler rollers 24 press belt 20 against the rear faces of guides 16. Preferably idler rollers 24 and guide rollers 22 are spaced around path 13 at angular locations such that needle 14 always passes between at least 2 of idler rollers 24 and/or guide rollers 22 and guides 16.

Belt 20 forms a closed loop passing around a drive pulley 28 and a tensioning roller 30. Preferably belt 20 is short. If belt 20 is very long then stretching of belt 20 may adversely affect the performance of suturing device 10. It is important that belt 20 not slip on drive pulley 28. Consequently, there should be a positive engagement (as opposed to an engagement that is solely frictional) between belt 20 and drive pulley 28. A positive engagement may be provided, for example, by providing projections on belt 20 which engage in indentations in drive pulley 28 or vice versa.

Belt 20 is preferably a toothed polyisoprene or polyurethane timing belt reinforced with polyester cords of the general type available from the Stock Drive Products Division of Designatronics Inc. of New Hyde Park, N.Y. Where, as is highly preferred, belt 20 is a toothed belt then drive pulley 28 has mating teeth. There must be a sufficiently positive engagement between drive pulley 28 and belt 20 to circulate belt 20 around its path even when needle 14 provides resistance to the motion of belt 20.

The leading edges 50 of guides 16 are bent slightly to form a channel for receiving the point of needle 14 and directing needle 14 along slit 17. Preferably the trailing edges of guides 16 are similarly bent to receive the rear end of needle 14 in the event that it is necessary to reverse the direction of needle 14.

The tension in drive belt 20 can be adjusted by moving tensioning roller 30 toward or away from opening 12 on sliding bracket 32. Sliding bracket 32 may be locked in place by a screw 33 or by any other practical locking means. By moving tension roller 30 toward opening 12 the tension in belt 20 is increased. By moving tension roller 30 away from opening 12 the tension in belt 20 is decreased.

Needle 14 is prevented from slipping in respect of belt 20 because the tension in belt 20 and the contact forces applied by idler rollers 24 and/or guide rollers 22 act together to keep belt 20 in firm frictional contact with needle 14. Needle 14 may be similar to a standard curved surgical needle having a smooth outer surface except that needle 14 preferably extends around an arc of about 240°, as described above, which is more than most standard curved surgical needles. The outer surface of needle 14 is preferably smooth and does not require any special treatment.

Figure 6A:
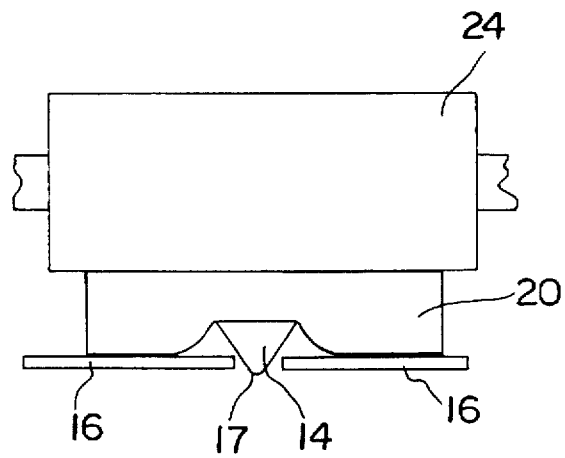
FIGS. 6A and 6B are schematic cross sectional views of two types of needle in a suturing device according to the invention.
Figure 6B:
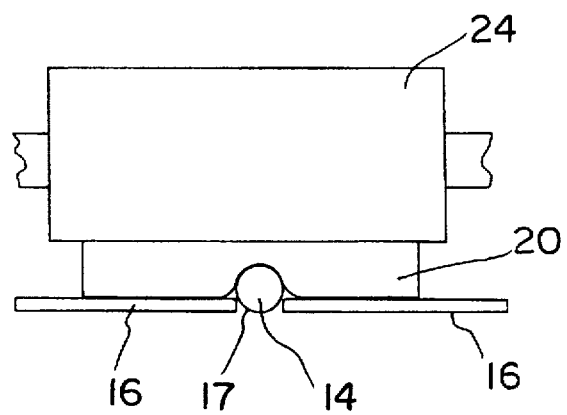

Needle 14 preferably has either a triangular cross section, as shown in FIG. 6A, or a circular cross section, as shown in FIG. 6B, so that needle 14 is readily guided along slit 17 between guides 16 as it is circulated around path 13.

Guides 16 are preferably made of a stiffly resilient material such as thin curved sheets of stainless steel. The clearance between idler rollers 24 and the rear faces of guides 16 is preferably less than the sum of the thicknesses of needle 14 and belt 20 so that belt 20 is compressed as needle 14 passes between each of rollers 24 and guides 16. Preferably, belt 20 is deformed so that its thickness is compressed by an amount in the range of about 10% to about 20% or 25% as needle 14 passes between each of rollers 24 and guides 16. Therefore, when needle 14 passes between an idler roller 24 and guides 16 needle 14 is firmly gripped.

For example, in a prototype suturing device, guides 16 were fabricated from stainless steel 0.35 mm thick, the clearance between idler rollers 24 and guides 16 was 2 mm, the thickness of belt 20 was 1.2 mm and the thickness of needle 14 was 1 mm and the slit between guides 16 was 0.5 mm wide. In the prototype, the radius of curvature of needle 14 and guides 16 was 9 mm.

Drive pulley 28 is driven by any suitable driving means capable of controllably and reversibly turning drive pulley 28. Preferably the driving means comprises a pair of bevel gears 42, 44. Gear 42 is turned by a drive shaft 40 which extends longitudinally of body 11. Gear 44 is attached to drive pulley 28. Turning bevel gear 42 in the direction of arrow 46 circulates needle 14 around opening 12 point first. The direction of rotation of shaft 40 may be reversed to cause needle 14 to circulate around opening 12 in the opposite direction. Thus, a surgeon can reverse the direction of motion of needle 14 if, for example, a stitch has been started in the wrong place.

Drive shaft 40 may be driven in any known manner. For example, drive shaft 40 may be driven by an electrical, mechanical, pneumatic or hydraulic actuator, such as a motor, equipped with suitable controls. In a preferred embodiment, drive shaft 40 is turned by a wheel 60 which is positioned so that it can be easily rotated by a surgeon's finger. Preferably the gearing of bevel gears 42 and 44 is such that two revolutions of wheel 60 causes needle 14 to circulate through one complete revolution. This provides the surgeon with precise reversible fingertip control over the motion of needle 14 yet reduces the force that the surgeon must apply to drive needle 14 around path 13.

As one of many possible alternatives to the use of a drive shaft 40 to turn drive pulley 28, drive pulley 28 could be at an end of body 11 remote from opening 12 and belt 20 could be long enough to extend around drive pulley 28 and around opening 12. Pulley 28 could then be driven directly by a driving means of any suitable type known to those skilled in the art of designing suturing devices.

Preferably suturing device 10 is equipped with a tissue holding means (indicated generally by 70) for holding tissues to be sutured. Tissue holding means 70 preferably comprises a pair of tissue gripping jaws 72 pivotally linked to suturing device 10. Jaws 72 hold tissues in place so that the tissues are not pushed away by needle 14 during suturing. Jaws 72 preferably close in opening 12 immediately behind the path 13 of needle 14.

Figure 4:
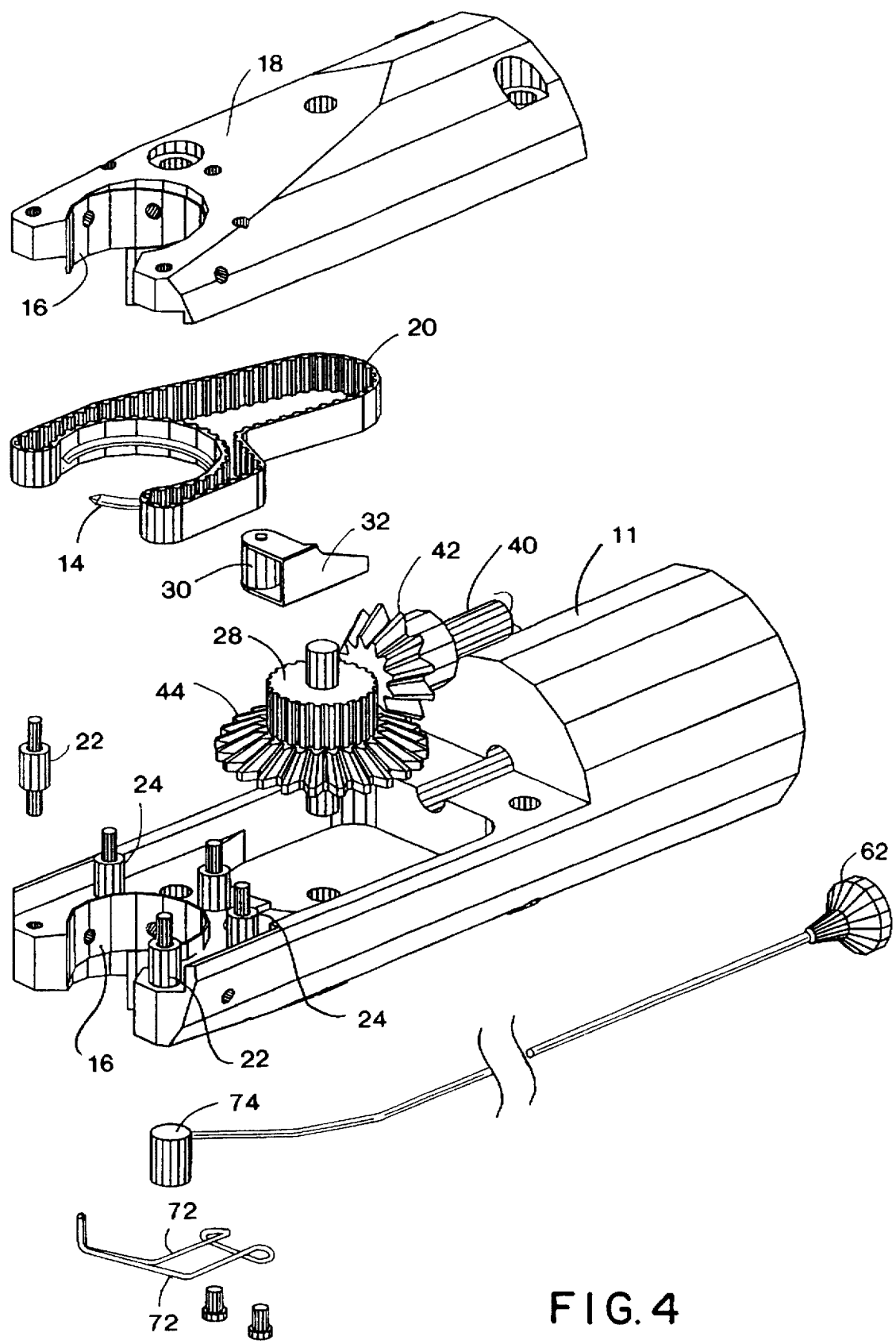
FIG. 4 is an exploded view of the suturing device of FIG. 1.
Figure 5:
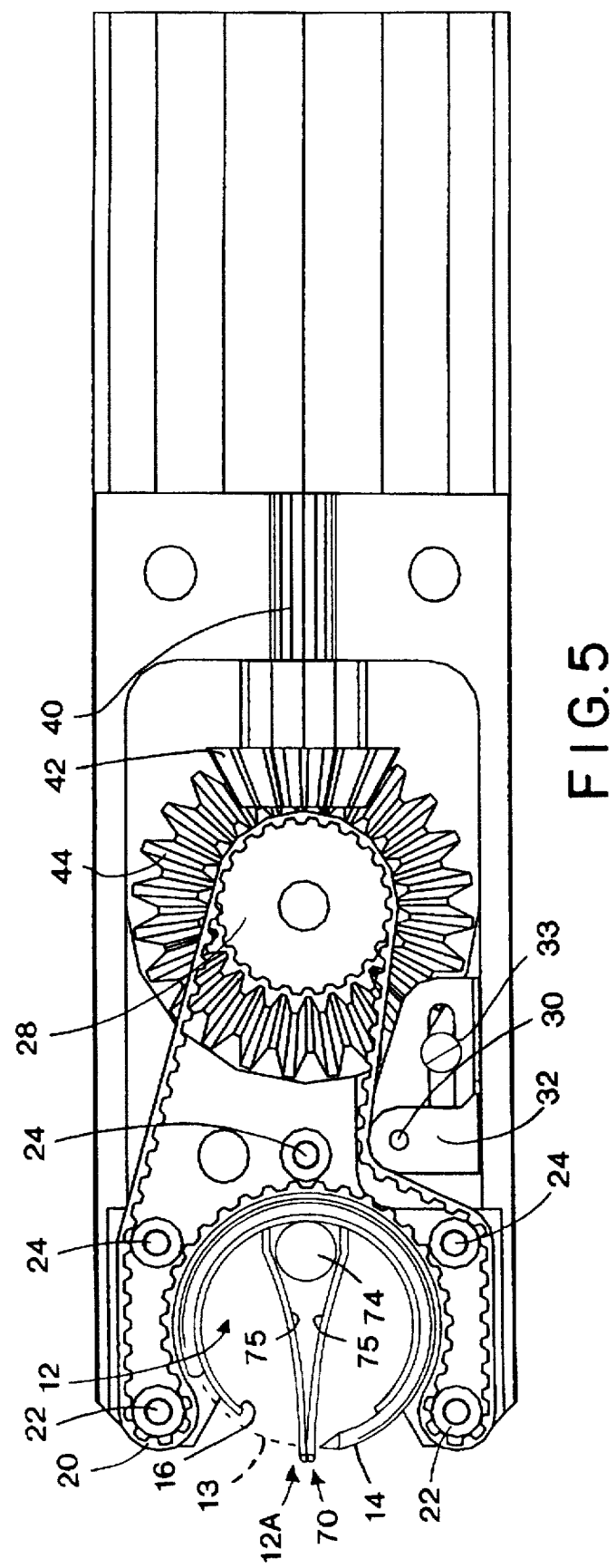
FIG. 5 is a longitudinal partially cut away view showing the internal workings of the suturing device of FIG. 1.

Suitable operating means are preferably provided to allow a user to open and close jaws 72. For example, as best shown in FIGS. 4 and 5, jaws 72 may be resilient and biased toward each other. For example, jaws 72 may be formed from spring wires. A wedge member 74 may be provided between angled inner edges 75 on each of jaws 72. Jaws 72 may be opened by moving wedge member 74 along jaws 72 to wedge jaws 72 apart. Jaws 72 may be closed by moving wedge member 74 in the opposite direction to allow jaws 72 to move together. This mechanism is preferred and is considered to be inventive by the inventors. However, it will be readily understood by any person skilled in the art of designing surgical instruments that there are numerous possible alternative mechanisms for moving one or both of jaws 72 to selectively place jaws 72 in either an open position or a closed position.

Figure 7A:
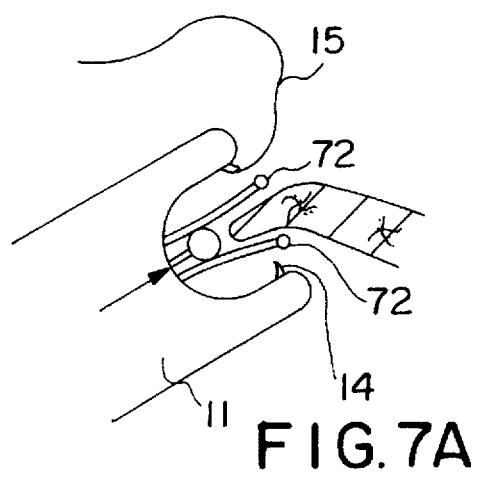
FIG. 7A, 7B, and 7C, illustrate a sequence of steps in applying a suture with a suturing device according to the invention; and, FIGS. 8A, 8B, and 8C illustrate the sequence of steps in one method for tying a knot in a piece of suture material with the suturing device of the invention.
Figure 7B:
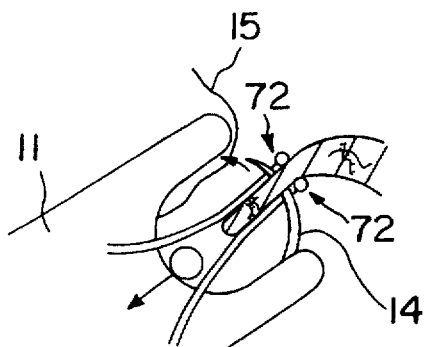
Figure 7C:
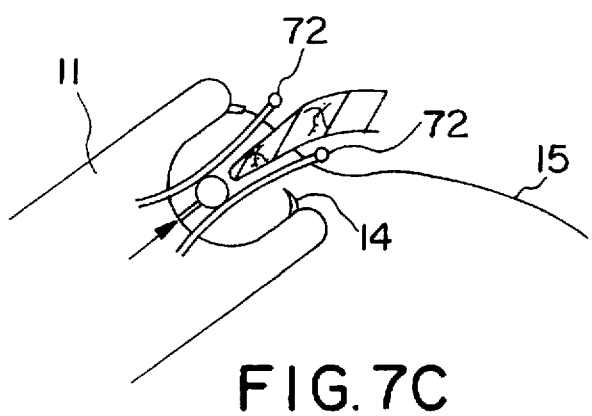

The operation of suturing device 10 is illustrated schematically in FIGS. 7A through 7C. As shown in FIG. 7A, a surgeon first opens jaws 72, then, as shown in FIG. 7B, the surgeon grasps the edges of a first piece of tissue to be sutured to a second piece of tissue with jaws 72 and operates needle 14 to pierce the first piece of tissue being sutured.

Then, as shown in FIG. 7C, the surgeon continues to circulate needle 14 until it has passed completely through the first piece of tissue to be sutured, and has drawn a length of suture material 15 through the tissue. Finally the surgeon opens jaws 72 to release the first piece of tissue and repeats the above steps for the second piece of tissue before forming a knot in suture material 15 to hold the two pieces of tissue together.

Figure 8A:
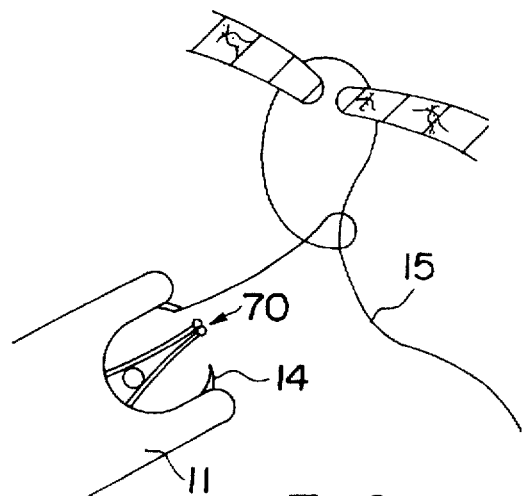
Figure 8B:
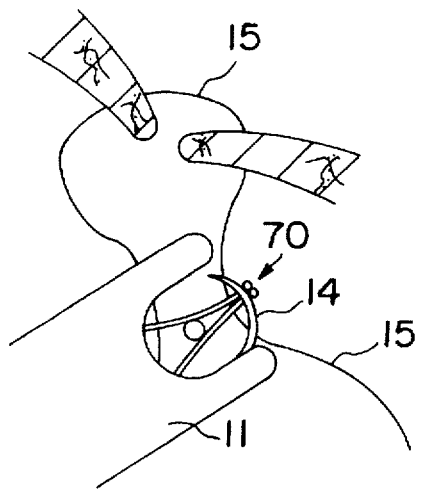
Figure 8C:
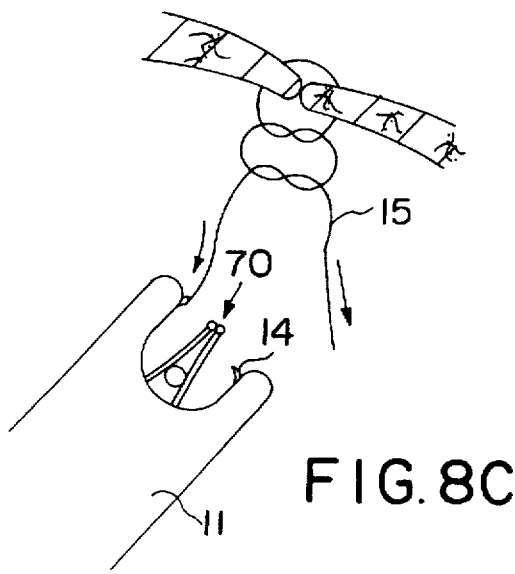

FIGS. 8A through 8C illustrate one method of using suturing device 10 to form a knot in suture material 15. As shown in FIG. 8A, opening 12 of suturing device 10 is placed around the tail of suture material 15. Needle 14 is then rotated to create a first loop around the tail as a flat knot as shown in FIG. 8B. This step is repeated to form a square knot as shown in FIG. 8C. Finally, the two ends of suture material 15 are pulled to tighten and secure the knot and suture material 15 is cut.

Suturing device 10 may be constructed in various ways. In the suturing device 10 depicted in the accompanying drawings, opening 12 is on the extreme end of body 11 facing along the axis of body 11. Opening 12 could be offset through an angle to face more to one side. In some circumstances, this could make it easier for a surgeon to see needle 14 as suturing device 10 is used.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

We claim:

1. A suturing device comprising:
   (a) a body having an opening therein and a pair of arcuate guides separated by a narrow slit, said guides subtending an angle greater than about 200 degrees in said opening;
   (b) a first guide roller near a first end of said guides;
   (c) a second guide roller near a second end of said guides;
   (d) a drive pulley;
   (e) a belt passing around said first and second rollers and positively engaged with said drive pulley, said belt having an outer surface in pressing engagement with rear faces of said guides;
   (f) an arcuate suturing needle having a common arc with said guides, said suturing needle received between said belt and said guides and having an outer surface frictionally engaged with said outer surface of said belt; and,
   (g) means for circulating said belt to circulate said suturing needle around a path.

2. The suturing device of claim 1 comprising at least one idler roller between said guide rollers for further compressing said belt against said rear faces of said guides.

3. The suturing device of claim 2 wherein said at least one idler roller and said guide rollers are spaced about said path at angular positions such that said needle passes adjacent at least two of said idler and guide rollers at every position of said needle along said path.

4. The suturing device of claim 3 wherein said belt is resiliently deformable in thickness and a spacing between said guides and said at least one idler roller is less than a sum of a thickness of said belt and a thickness of said needle.

5. The suturing device of claim 4 wherein said belt thickness is compressed in the range of 10% to 25% by passage of said needle between said idler rollers and said guides.

6. The suturing device of claim 5 wherein said needle has a triangular cross section having a radially inwardly pointing vertex and said radially inwardly pointing vertex is received in said slit between said guides.

7. The suturing device of claim 5 wherein said needle is circular in cross section.

8. The suturing device of claim 5 wherein said belt has a toothed inner surface and said drive pulley has teeth in meshing engagement with teeth on said belt inner surface.

9. The suturing device of claim 8 wherein said means for circulating said belt comprises a bevel gear on said drive pulley in meshing engagement with a second bevel gear, said second bevel gear connected to a drive-rod extending longitudinally in said body.

10. The suturing device of claim 9 wherein said means for circulating said belt comprises a drive wheel at an end of said body remote from said opening and mechanically linked to said drive pulley wherein rotation of said drive wheel drives rotation of said drive pulley.

11. The suturing device of claim 10 wherein said needle and said guides each subtend angles greater than 230°.

12. The suturing device of claim 11 wherein said belt comprises a material selected from the group consisting of reinforced polyisoprene and reinforced polyurethane.

13. The suturing device of claim 11 comprising a pair of tissue gripping jaws supported in said opening, said jaws having an open position wherein said jaws are spaced apart and a closed position wherein said jaws are pressed together adjacent said path.

14. The suturing device of claim 2 wherein said belt is resiliently deformable in thickness and a spacing between said guides and said at least one idler roller is less than a sum of an uncompressed thickness of said belt and a thickness of said needle.

15. The suturing device of claim 14 wherein said belt thickness is compressed in the range of 10% to 25% from said uncompressed thickness by passage of said needle between said idler rollers and said guides.

16. The suturing device of claim 15 wherein said at least one idler roller has a hard incompressible surface bearing on said belt.

17. The suturing device of claim 1 wherein said needle and said guides each subtend angles greater than 230°.

18. The suturing device of claim 1 wherein said body is elongated and cylindrical and said opening is at one end of said body.

19. The suturing device of claim 18 comprising a pair of tissue gripping jaws supported in said opening, said jaws having an open position wherein said jaws are spaced apart and a closed position wherein said jaws are pressed together adjacent said path and operating means to selectively move said jaws between said open and closed positions.

20. The suturing device of claim 19 wherein said operating means comprises bias means biasing said jaws toward said closed position.

21. The suturing device of claim 20 wherein said operating means comprises a wedge member engaged between angled edge surfaces on said jaws wherein displacing said wedge member in a first direction moves said jaws toward said open position and moving said wedge member in a second direction allows said jaws to move toward said closed position.

22. A method for making and knotting a suture, said method comprising the steps of:
   (a) providing a suturing device comprising:
      (i) a pair of arcuate guides separated by a narrow slit;
      (ii) a belt having an outer surface in pressing engagement with rear faces of said guides; and, (iii) an arcuate suturing needle having a common arc with said guides, said suturing needle received between said belt and said guides and having an outer surface frictionally engaged with said outer surface of said belt;

(b) providing a length of suture material affixed to said needle;

(c) circulating said belt to cause an end of said suturing needle to pierce and pass from a first side to a second side through a thing to be sutured;

(d) continuing to circulate said belt to cause said needle to draw said suture material along said slit between said guides until said suture material exits said slit and passes through said thing to be sutured; and, (e) forming a loop around a portion of said suturing material on said first side of said thing to be sutured by continuing to circulate said belt to cause said needle to advance around said portion of said suturing material and to draw said suture material along said slit between said guides until said suture material exits said slit and passes around said portion of suture material.

* * * * *